United States Patent [19]

Kio

[11] Patent Number: 5,400,664
[45] Date of Patent: Mar. 28, 1995

[54] APPARATUS FOR OBSERVING THE SUCTION OF A SAMPLE HAVING AN AUTOMATIC REGULATION FUCTION

[75] Inventor: Katsuhiko Kio, Kobe, Japan

[73] Assignee: Toa Medical Electronics Co., Ltd., Kobe, Japan

[21] Appl. No.: 918,764

[22] Filed: Jul. 27, 1992

[30] Foreign Application Priority Data

Aug. 26, 1991 [JP] Japan .................. 3-075145 U

[51] Int. Cl.⁶ .............................................. G01N 1/14
[52] U.S. Cl. .................. 73/863.01; 73/864.73; 250/565
[58] Field of Search ........... 73/863.01, 863.02, 863.03, 73/864.34, 864.35, 864.73, 864.74, 61.48, 64.56, 864.11, 864.12, 864.14, 864.15, 864.21, 864.22–864.25; 250/564, 565; 356/39, 40, 41, 42, 244, 246

[56] References Cited

U.S. PATENT DOCUMENTS

| | | | |
|---|---|---|---|
| 2,147,422 | 2/1939 | Bendz | 250/564 X |
| 3,424,557 | 1/1969 | Skeggs | 73/863.01 X |
| 4,522,493 | 6/1985 | Tamagawa et al. | 250/564 X |
| 4,675,301 | 6/1987 | Charneski et al. | 73/863.01 X |
| 4,683,212 | 7/1987 | Uffenheimer | 73/863.01 X |
| 4,794,806 | 1/1989 | Nicoli et al. | 73/863.01 |
| 4,829,837 | 5/1989 | Telfer | 73/863.01 |
| 4,893,515 | 1/1990 | Uchida | 73/864.34 |

FOREIGN PATENT DOCUMENTS

| | | | |
|---|---|---|---|
| 29769 | 3/1980 | Japan | 73/863.01 |
| 225633 | 10/1986 | Japan | 73/863.01 |
| 293444 | 11/1988 | Japan | . |
| 91039 | 4/1989 | Japan | . |
| 61577 | 3/1990 | Japan | 73/863.01 |
| 1265520 | 10/1986 | U.S.S.R. | 73/863.01 |

Primary Examiner—Tom Noland
Attorney, Agent, or Firm—Jones, Tullar & Cooper

[57] ABSTRACT

In an automatic analyzer such as blood analyzer, it is important to observe whether the sample, such as a blood sample, is sucked correctly or not. In an apparatus for observing suction of a sample, comprising a sample suction tube, a luminous element for emitting light toward the sample suction tube being driven by a driving circuit, a photo sensor for receiving the light from the sample suction tube, and a judging circuit for judging the sample suction on the basis of the signal from the photo sensor, a controller is provided in order to drive the luminous element so that the output (Vp) of the photo sensor may be nearly the reference value (Vr) before a sample suction, and to drive the luminous element so as to hold the driving state during the sample suction. Thus, the sensitivity adjustment of the apparatus for observing suction of a sample may be automated, and the observing capability of the apparatus is enhanced.

3 Claims, 4 Drawing Sheets

APPARATUS FOR OBSERVING THE SUCTION OF A SAMPLE HAVING AN AUTOMATIC REGULATION FUCTION

BACKGROUND OF THE INVENTION

The present invention relates to an apparatus for observing the suction (aspiration) of a sample (liquid specimen) in an automatic analyzer such as a blood analyzer, and more particularly to an apparatus for observing the suction of a sample having an automatic regulation function for maintaining a favorable detection sensitivity.

Hitherto apparatuses have been known for observing whether a sample, such as a blood sample, is aspirated correctly or not. FIG. 1 shows an example thereof, which is intended to observe the suction of a sample by the change of transmitting light from a photo element.

Numeral 14 denotes a tube for sucking (aspirating) a sample, which is made of a synthetic resin of high transparency. A luminous element 10 such as an LED and a photo sensor 12 such as a photo transistor are disposed opposingly across the sample suction tube 14. A constant current circuit 16 composed of a transistor 18 and a resistance R3 is connected to the luminous element 10. A variable resistor VR is connected to the base B of the transistor 18, and the value of the current flowing in the luminous element 10 is varied by adjusting the variable resistor VR.

On the other hand, resistors R2, R1 are connected to the collector C and emitter E of the photo sensor 12, and the current corresponding to the quantity of light received that has been detected is converted into a voltage and taken out. The resistance R2 is not necessarily required. To the output of the photo sensor 12 is connected a judging circuit 20 for judging whether the sample suction is normal or abnormal depending on the change of the quantity of light transmitted at the time of suction of the sample.

Initially, the sample suction tube 14 is filled up entirely with a cleaning solution, and an air layer is provided at the front end of the tube. The portion of the sample suction tube 14 where the luminous element 10 and photo sensor 12 are disposed is high in transparency, the light transmits well, and the voltage Vp at test point Vp is high. By suction of the sample, when the blood reaches the observing area, the light is shielded by the blood corpuscle components, and the detected voltage Vp becomes low. By a comparator (not shown) in the judging circuit 20, the detected voltage Vp is set in a binary value showing whether the blood is sucked (aspirated) or not. On the basis of the binary signal, it is further judged whether the suction is normal or not. When the sample suction is over, the cleaning solution is poured into the tube, and the residue of the blood sample is washed away.

In this apparatus, incidentally, various fluctuations (scatter) occur. For example, fluctuations of the circuit components, such as the luminous element and the photo sensor, and fluctuations of the tube diameter and transparency are known. In order to maintain a high detection capability by absorbing such fluctuations, it is designed to adjust the current of the luminous element 10 by the variable resistor VR. In this adjustment, it is designed so that the detection voltage Vp at the test point TP may be a specified value in the specific conditions of the state in the sample suction tube 14 (for example, with the tube filled up with a clear liquid).

The existing apparatus had the following problems.

(1) Every time the tube is exchanged, the current of the luminous element must be adjusted by the VR depending on the tube diameter and transparency, and the operation is complicated.
(2) The characteristics of the circuit components vary with the passing of time and change of temperature, and the detection sensitivity is lowered.
(3) The detection sensitivity is also lowered by the contamination of tube or occurrence of injury.
(4) In the case of a thin tube, a slight deviation of position of the tube, or dislocation of the luminous element or the photo sensor may lead to lowering of the detection sensitivity.

OBJECT AND SUMMARY OF THE INVENTION

It is hence a primary object of the present invention to provide an apparatus for observing the suction of a sample capable of always maintaining a favorable detection sensitivity by automatic regulation.

To achieve the above object, the present invention is embodied as an apparatus for observing the suction of a sample having the function of automatic regulation comprising a sample suction tube, a luminous element driven by a driving circuit for emitting light toward the sample suction tube, a photo sensor for receiving the light from the sample suction tube, and a judging circuit for judging the suction of the sample on the basis of the signal from the photo sensor, wherein control means is further disposed to drive the luminous element so that the output of the photo sensor may be nearly the reference (standard) value before suction of the sample, and to drive the luminous element to hold the driving state when sucking the sample.

In this case, the control means comprises means for generating a reference value, an amplifying circuit for receiving the output of the photo sensor in one input part and receiving the reference voltage in another input part, and amplifying the difference of the two, and a sample hold circuit composed of switch means having one end connected to the output of the amplifying circuit to be turned on before suction of a sample and turned off at the time of suction of the sample, a capacitor connected to the other end of the switch means, and a buffer circuit having the other end of the switch means and capacitor connected to the input part, and the driving circuit of the luminous element connected to the output part.

Also the control means comprises an A/D conversion circuit connected to the output of the photo sensor, data processing means connected to the A/D conversion circuit, and a D/A conversion circuit connected between the data processing means and driving circuit, in which the data processing means comprises means for setting a reference value, means for calculating the value corresponding to the difference between the output value of the photo sensor and the reference value, and holding means for operating the above calculation before suction of a sample to supply the data into the D/A conversion circuit, and prohibiting the calculation at the time of suction of a sample to hold the data before suction of a sample to supply into the D/A conversion circuit.

When the sample is sucked into the sample suction tube, light is emitted from the luminous element toward the sample suction tube, and the quantity of light entering the photo sensor by passing through the sample suction tube varies, and this change is detected by the photo sensor, and it is judged whether the sample is sucked or not, and whether the suction of a sample is normal or not in the judging circuit. At this time, the control means drives the luminous element so that the output of the photo sensor may be nearly the reference value before sample suction, and drives the luminous element so as to hold the driving state during sample suction.

DETAILED DESCRIPTION OF THE PREFERRED EMBODIMENTS

Figure 1:
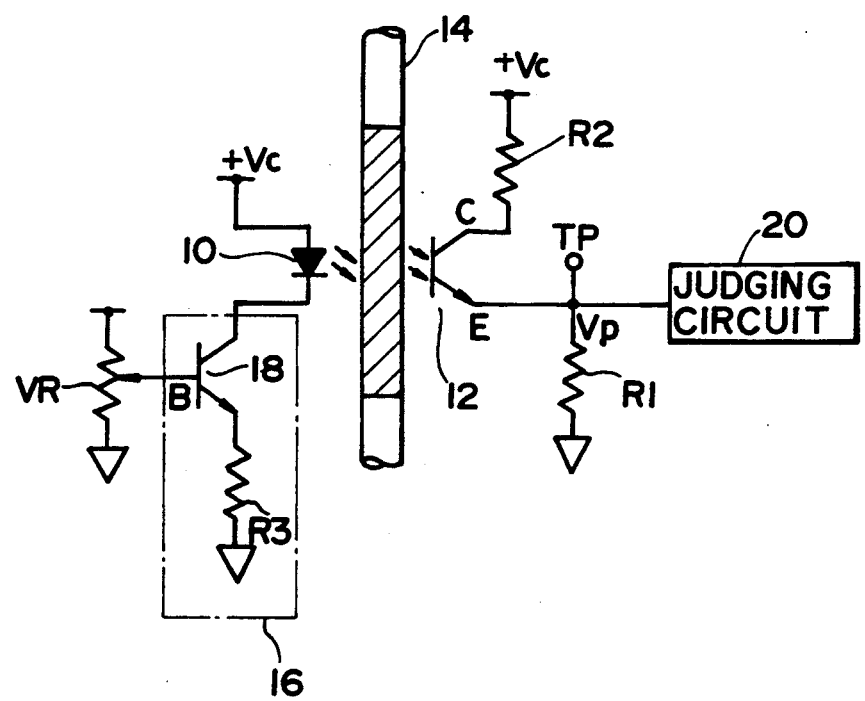
FIG. 1 is a schematic structural diagram showing an example of a conventional apparatus for observing the suction of a sample.

Referring now to the drawings, some of the preferred embodiments of the present invention are described in detail below.

Figure 2:
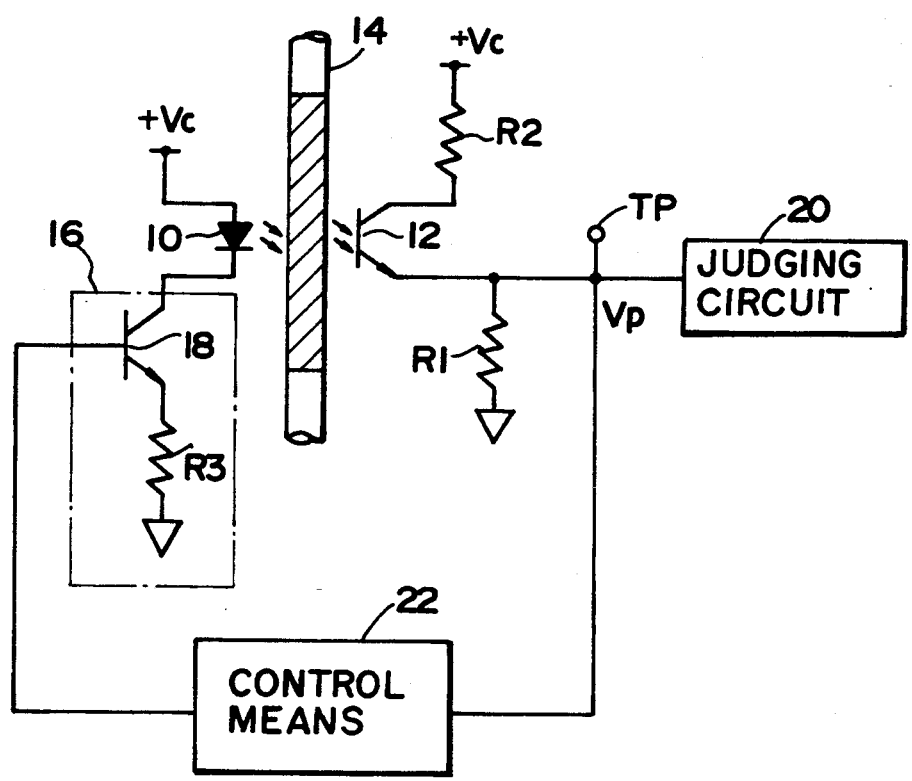
FIG. 2 is a schematic structural diagram showing an embodiment of an apparatus for observing the suction of a sample having an automatic regulation function according to the present invention.

The present invention presents, as shown in FIG. 2, an apparatus for observing the suction of a sample having an automatic regulation function, comprising a sample suction tube 14, a luminous element 10 driven by a driving circuit 16 for emitting light toward the sample suction tube 14, a photo sensor 12 for receiving the light from the sample suction tube 14, and a judging circuit 20 for judging the suction of a sample on the basis of the signal from the photo sensor 12, wherein control means 22 is further disposed to drive the luminous element 10 so that the output Vp of the photo sensor 12 may be nearly the reference (standard) value Vr before suction of a sample, and to drive the luminous element 10 to hold the driving state when sucking the sample.

Figure 3:
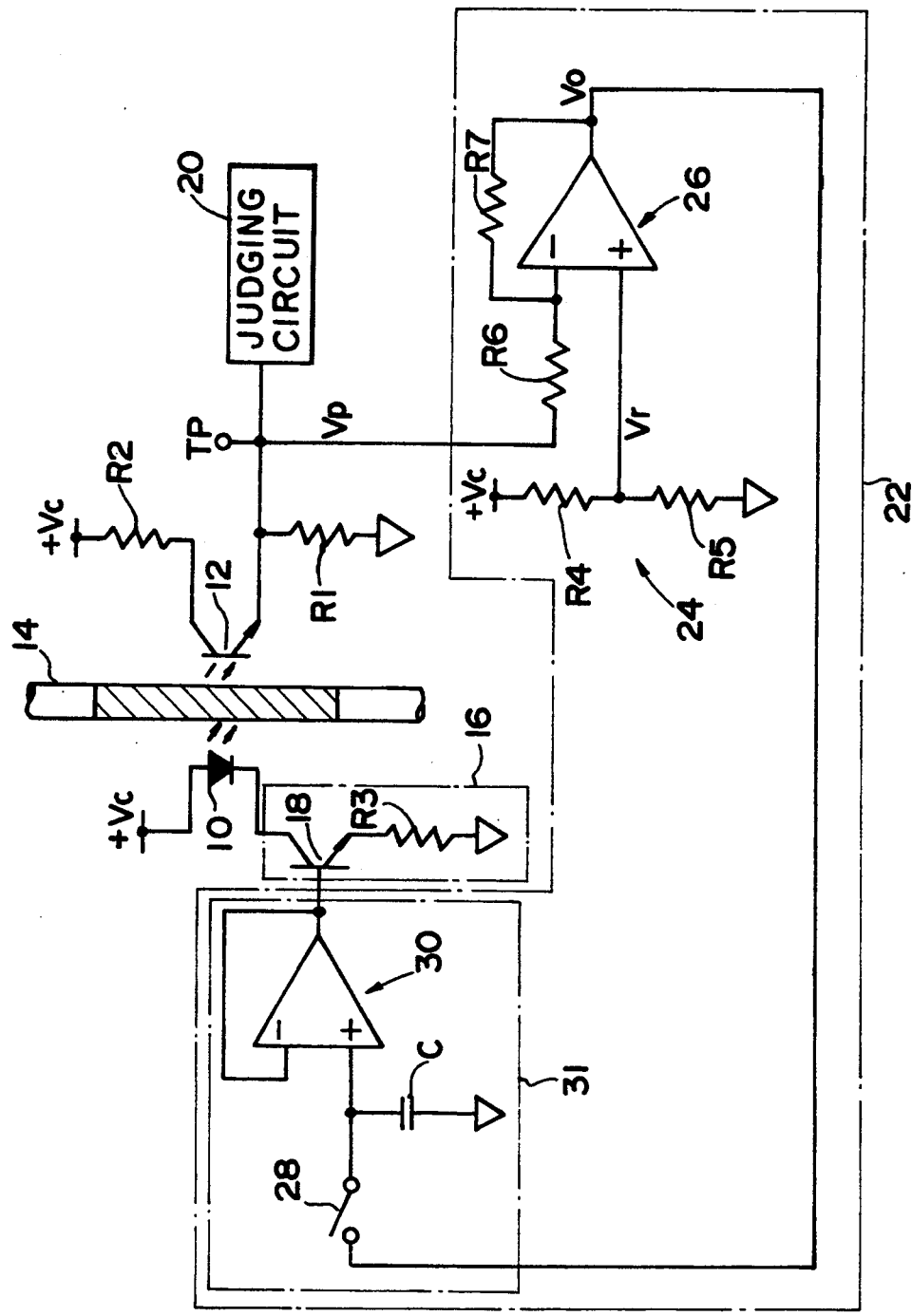
FIG. 3 is a schematic structural diagram showing an embodiment specifically depicting the control means in the apparatus in FIG. 2.

In this case, as shown in FIG. 3, the control means 22 comprises means 24 for generating the reference value Vr, an amplifying circuit 26 for receiving the output of the photo sensor 12 at one input part and receiving the reference voltage Vr at the other input part, and amplifying the difference of the two, and a sample hold circuit 31 composed of switch means 28 having one end connected to the output of the amplifying circuit 26 to be turned on before suction of a sample and turned off at the time of suction of the sample, a capacitor C connected to the other end of the switch means 28, and a buffer circuit 30 having the other end of the switch means 28 and capacitor C connected to the input part, and the driving circuit 16 of the luminous element 10 connected to the output part.

Figure 4:
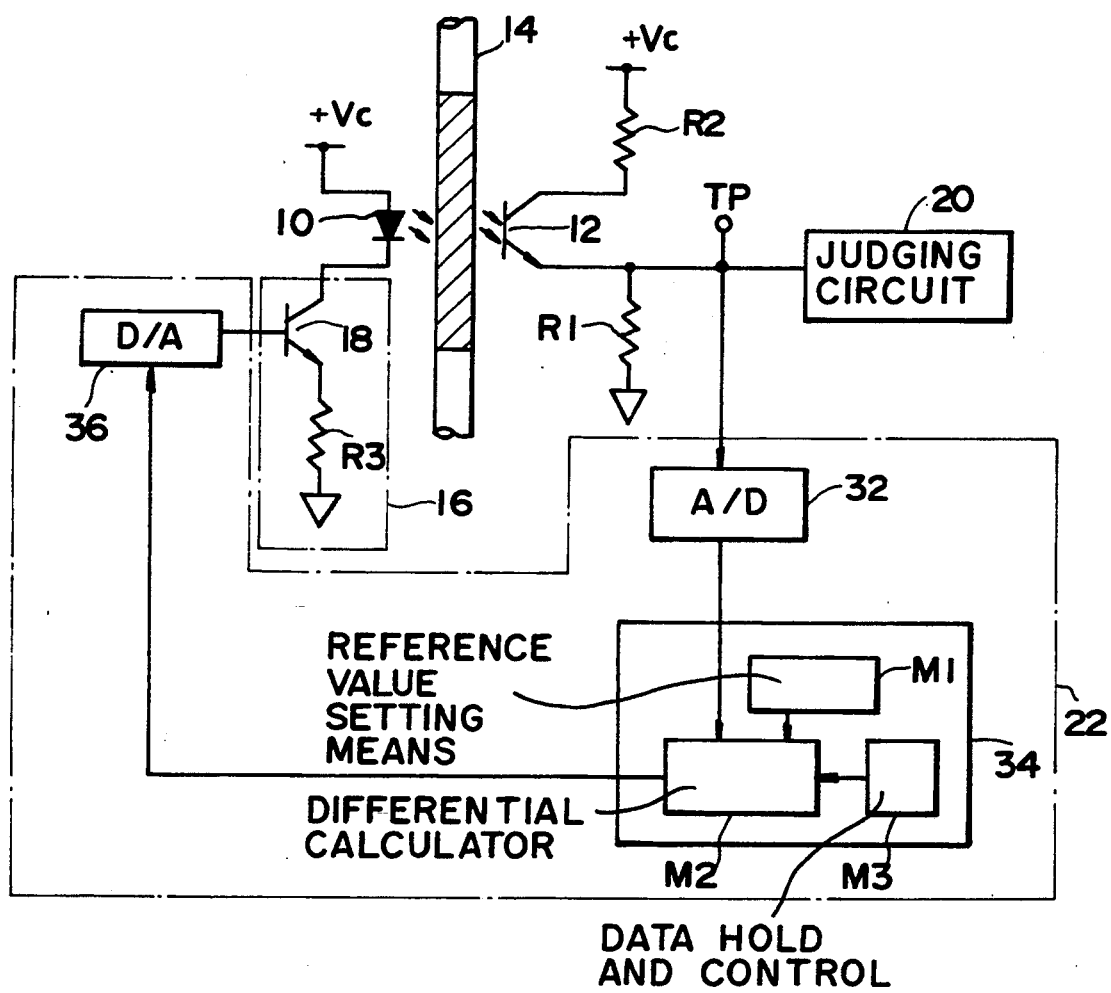
FIG. 4 is a schematic structural diagram showing another embodiment specifically depicting control means in the apparatus in FIG. 2

Also the control means 22 comprises, as shown in FIG. 4, an A/D conversion circuit 32 connected to the output of the photo sensor 12, data processing means 34 connected to the A/D conversion circuit 32, and a D/A conversion circuit 36 connected between the data processing means 34 and driving circuit 16, in which the data processing means 34 comprises means M1 for setting the reference value, means M2 for calculating the value corresponding to the difference between the output value of the photo sensor 12 and the reference value, and holding means M3 for operating the above calculation before suction of a sample to supply the data into the D/A conversion circuit 36, and prohibiting the calculation at the time of suction of the sample to hold the data before suction of the sample to supply into the D/A conversion circuit 36.

When the sample is sucked (aspirated) into the sample suction tube 14, light is emitted from the luminous element 10 toward the sample suction tube 14, and the quantity of light passing through the sample suction tube 14 and entering the photo sensor 12 varies. This change is detected by the photo sensor 12, and it is judged whether the sample is sucked or not, and whether the suction of the sample is normal or not in the judging circuit 20. At this time, the control means 22 drives the luminous element 10 so that the output Vp of the photo sensor 12 may be nearly the reference value Vr before a sample suction, and drives the luminous element 10 so as to hold the driving state during the sample suction.

Embodiment 1

In FIG. 2, numeral 16 is a constant current driving circuit for driving the luminous element 10 at a specified current. In this embodiment, omitting the variable resistor VR in FIG. 1, there is control means 22 for automatically setting the current value of the constant current driving circuit 16 at a specified value depending on the output voltage Vp of the photo sensor 12. Numeral 14 denotes the sample suction (aspiration) tube, 18 is the transistor, and 20 is the judging circuit.

The control means 22 drives the constant current driving circuit 16 for radiating the luminous element 10 so that the output Vp of the photo sensor 12 may be close to the reference value Vr in the state before suction of a sample, and drives the constant current driving circuit 16 so as to maintain the luminous state during the sample suction.

Embodiment 2

In this embodiment, as shown in FIG. 3, the control means 22 comprises an analog circuit.

Numeral 24 represents means for generating the reference value Vr, in which the supply voltage Vc is divided by resistances R4, R5. It may also be generated by another constant voltage circuit. The differential amplifying circuit 26 amplifies the difference of the reference value Vr and output Vp of the photo sensor 12. The output Vp of the photo sensor 12 is entered in an inverting input terminal (−) of the amplifying circuit 26, and the reference voltage Vr is entered at the non-inverting input terminal (+), and the difference of the two is amplified. One end of switch means 28 is connected to the output of the amplifying circuit 26. A capacitor C for accumulating charge is connected to the other end of the switch means 28. The other end of the capacitor C is connected to ground. The capacitor C is further connected with a buffer circuit 30 of high input impedance. A sample hold circuit 31 is composed of the switch means 28, capacitor C and buffer circuit 30. The sample state occurs when the switch means 28 is ON, and the hold state when it is OFF.

Before the suction of a sample, the inside of the sample suction tube 14 in the observing region is filled with a cleaning solution. In this state, the apparatus is controlled automatically. Before the suction of a sample, the switch means 28 is turned on, and when sucking the sample, the switch means 28 is turned off. On/off switching of the switch means 28 is controlled from outside.

Next the operation of the circuit is explained. The output Vo of the amplifying circuit 26 is expressed by the following formula.

$$Vo = Vr - (Vp - Vr) * R7/R6$$

However, the output Vo is in a range of 0 to Vc*R1/(R1+R2). Here Vo is supposed to be 12[V], and the reference value Vr about 9[V]. The resistance R7 has a larger value than R6. For example, R6=1[kohm], R7=100[kohms].

Suppose the switch means 28 is OFF, with no charge accumulated in the capacitor C and no current flowing in the luminous element 10, thereby not emitting light. In this state, the output Vp of the photo sensor 12 is almost 0[V]. When the switch means 28 is turned on, the output Vo becomes the upper limit value as known from the formula above, and the output of the buffer circuit 30 increases. As the base potential of the transistor 18 in the constant current driving circuit 16 goes up, the current in the luminous element 10 increases to increase the quantity of light emitted, and the output voltage Vp of the photo sensor 12 increases. If, however, the output Vp rises too high, the output Vo descreases, the base potential declines, the current decreases, the quantity of light emitted also decreases, and the output Vp drops. That is, the output Vp acts to, from a certain boundary point, raise if descending, and lower if ascending, thereby maintaining a certain stable value. Since the resistance R7 has a larger value than R6 as mentioned above, the output Vo changes largely if the output Vp changes slightly near the reference value Vr, so that the output Vp is stabilized at a value close to the reference value Vr. That is, the sensitivity is adjusted.

When the switch means 28 is turned off, the luminous element 10 emits light in a specific quantity regardless of the value of the output Vp by the function of the capacitor C. When a sample is sucked, a specified voltage is produced from the photo sensor 12 depending on the state of the portion being observed. Depending on the voltage it is judged whether suction is normal or not in the judging circuit 20. Incidentally, if the response of the control means 22 is too fast, the output Vp oscillates, and therefore it is necessary to delay the response. The capacitor C also plays this role, but another capacitor may be connected parallel to the resistance R7 of the amplifying circuit 26. Usually, the output of the control means 22 is in a certain specific range, and if out of that range, it means occurrence of some abnormality (such as injury to the tube), and it is further desired to observe the output continuously.

The other structure and its action are the same as in Embodiment 1.

Embodiment 3

As shown in FIG. 4, a digital circuit is used as the control means 22 in this embodiment.

The control means 22 comprises the A/D conversion circuit 32 connected to the output of the photo sensor 12, data processing means 34 such as a microcomputer connected to the A/D conversion circuit 32, and the D/A conversion circuit 36 connected between the data processing means 34 and driving circuit 16. In the data processing means 34, M1 is the reference value setting means (for example, memory means) for setting the reference value data (the value corresponding to the reference voltage Vr in FIG. 3), M2 is the calculating means for calculating the value corresponding to the difference between the output value data of the photo sensor 12 and the reference value data, and M3 is the holding means for causing the calculating means M2 to calculate as stated above before suction of a sample to make the output data of the photo sensor 12 equal to the reference value data on the basis of the result of the calculation, and for prohibiting the operation by the calculating means M2 to hold the value before a sample suction during the sample suction.

The other structure and its action are the same as in Embodiment 1.

Being thus composed, the present invention brings about the following effect.

(1) Sensitivity adjustment of an apparatus for observing suction of a sample may be automated in a simple construction, and various fluctuations of the apparatus may be absorbed to adjust to specified values. Whence, the labor of adjustment is saved, the observing capability of the apparatus is enhanced, and moreover the detection sensitivity is not lowered due to the passing of time or change of temperature or the like.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. An apparatus for observing suction of a sample, the apparatus having an automatic regulation function, comprising: a sample suction tube; a luminous element for emitting light toward the sample suction tube; a driving circuit defining a driving state for driving the luminous element; photo sensor means for receiving the light from the sample suction tube; a judging circuit connected to said photo sensor means for judging the suction of the sample on the basis of an output signal from the photo sensor means; and control means connected to said driving circuit, said photo sensor means and said judging circuit for driving said luminous element so that the output of said photo sensor means substantially equals a reference value before sample suction, and for driving said luminous element for holding said driving state during the sample suction.

2. The apparatus of claim 1, wherein said control means comprises means for generating said reference value, an amplifying circuit for receiving the output of said photo sensor means at one input part and receiving said reference value as a reference voltage at another input part, and amplifying the difference of the two, and a sample hold circuit including switching means having one end connected to an output of the amplifying circuit so as to be turned on before a sample suction and turned off during sample suction, a capacitor connected to another end of the switch means, and a buffer circuit having said another end of the switch means and the capacitor connected at an input part there of and said driving circuit connected at an output part thereof.

3. The apparatus of claim 1, wherein said control means comprises an A/D conversion circuit connected to the output of said photo sensor means, data processing means connected to the A/D conversion circuit, and a D/A conversion circuit connected between the data processing means and said driving circuit, in which the data processing means comprises means for setting said reference value, means for calculating the value corresponding to the difference between the output value of said photo sensor means and said reference value, and holding means for performing the calculation above before a sample suction to supply the data into the D/A conversion circuit, and prohibiting the operation during sample suction to hold the value before sample suction to supply into the D/A conversion circuit.

* * * * *

UNITED STATES PATENT AND TRADEMARK OFFICE
CERTIFICATE OF CORRECTION

PATENT NO. : 5,400,664
DATED : March 28, 1995
INVENTOR(S) : Katsuhiko Kio

It is certified that error appears in the above-indentified patent and that said Letters Patent is hereby corrected as shown below:

Claim 2, column 6, line 67, a "," should be deleted; and column 7, line 12, "there of" should be "thereof,".

Signed and Sealed this

Thirteenth Day of June, 1995

Attest:

BRUCE LEHMAN

*Attesting Officer*  *Commissioner of Patents and Trademarks*